United States Patent
Mozes et al.

(10) Patent No.: US 9,877,810 B2
(45) Date of Patent: Jan. 30, 2018

(54) METHOD FOR CONDUCTING A GUIDED SINUS LIFT PROCEDURE

(71) Applicant: Neocis Inc., Miami, FL (US)

(72) Inventors: Alon Mozes, Miami Beach, FL (US); Federico Grande, Stuart, FL (US)

(73) Assignee: Neocis Inc., Miami, FL (US)

( * ) Notice: Subject to any disclaimer, the term of this patent is extended or adjusted under 35 U.S.C. 154(b) by 896 days.

(21) Appl. No.: 13/836,091

(22) Filed: Mar. 15, 2013

(65) Prior Publication Data

US 2014/0272789 A1 Sep. 18, 2014

(51) Int. Cl.
| | |
|---|---|
| *A61C 8/00* | (2006.01) |
| *A61B 6/14* | (2006.01) |
| *A61B 34/00* | (2016.01) |
| *A61B 34/10* | (2016.01) |
| *A61B 17/17* | (2006.01) |
| *A61B 90/00* | (2016.01) |

(52) U.S. Cl.
CPC .............. *A61C 8/0092* (2013.01); *A61B 6/14* (2013.01); *A61B 17/1785* (2016.11); *A61B 34/10* (2016.02); *A61B 34/76* (2016.02); *A61B 2090/363* (2016.02)

(58) Field of Classification Search
CPC . A61B 17/17; A61B 17/1703; A61B 17/1739; A61B 17/1785; A61B 19/50; A61C 8/0089; A61C 8/0092; A61C 1/082; A61C 1/084
See application file for complete search history.

(56) References Cited

U.S. PATENT DOCUMENTS

| | | | |
|---|---|---|---|
| 5,989,025 A * | 11/1999 | Conley | 433/76 |
| 8,262,665 B2 | 9/2012 | Massoud | |
| 8,308,727 B2 * | 11/2012 | Hernandez et al. | 606/86 R |
| 8,343,178 B2 | 1/2013 | Novak et al. | |
| 8,394,099 B2 * | 3/2013 | Patwardhan | 606/80 |
| 2005/0021142 A1 * | 1/2005 | Ganz et al. | 623/16.11 |
| 2005/0216024 A1 * | 9/2005 | Massoud | 606/87 |
| 2006/0142657 A1 * | 6/2006 | Quaid et al. | 600/424 |
| 2008/0161934 A1 * | 7/2008 | Yamada | A61B 17/1655 623/17.17 |
| 2009/0131941 A1 * | 5/2009 | Park et al. | 606/87 |

(Continued)

*Primary Examiner* — Christian Sevilla
*Assistant Examiner* — Eric S Gibson
(74) *Attorney, Agent, or Firm* — Womble Bond Dickinson (US) LLP

(57) ABSTRACT

A method of conducting a sinus lift procedure is provided. A secure and physical interaction is formed between a fiducial device and a site within a patient's mouth to form a fiducial marker. A virtual incising plan is formed for incising the patient's maxilla, with respect to the fiducial marker, for providing access to a sinus membrane. Movement of an incising device is physically regulated with respect to the fiducial marker with a guidance device. The incising device is in physical communication with the fiducial marker via the fiducial device. The guidance device physically regulates movement of the incising device, according to the virtual incising plan and corresponding with physical manipulation of the incising device by a user, to incise the maxilla. Tactile feedback is provided to the user, via the incising device, if the physical manipulation of the incising device by the user deviates from the virtual incising plan.

6 Claims, 8 Drawing Sheets

(56) References Cited

U.S. PATENT DOCUMENTS

Figure 1:
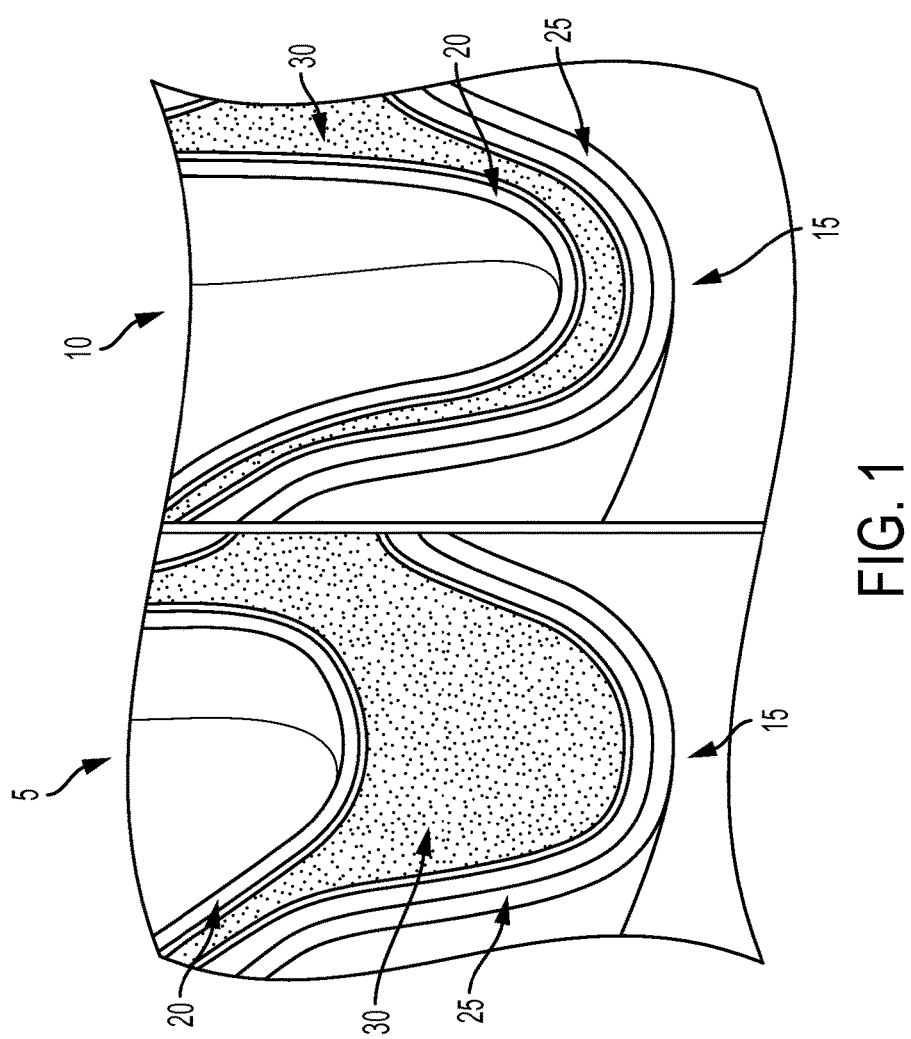

| | | | |
|---|---|---|---|
| 2009/0253095 A1* | 10/2009 | Salcedo et al. | 433/75 |
| 2010/0081914 A1* | 4/2010 | Waynik et al. | 600/407 |
| 2010/0179564 A1* | 7/2010 | Mitchell et al. | 606/130 |
| 2010/0191242 A1* | 7/2010 | Massoud | 606/87 |
| 2010/0311028 A1* | 12/2010 | Bell et al. | 434/263 |
| 2012/0230566 A1* | 9/2012 | Dean et al. | 382/131 |
| 2013/0150857 A1* | 6/2013 | Better | A61C 8/0022 606/80 |
| 2014/0272789 A1* | 9/2014 | Mozes et al. | 433/173 |

* cited by examiner

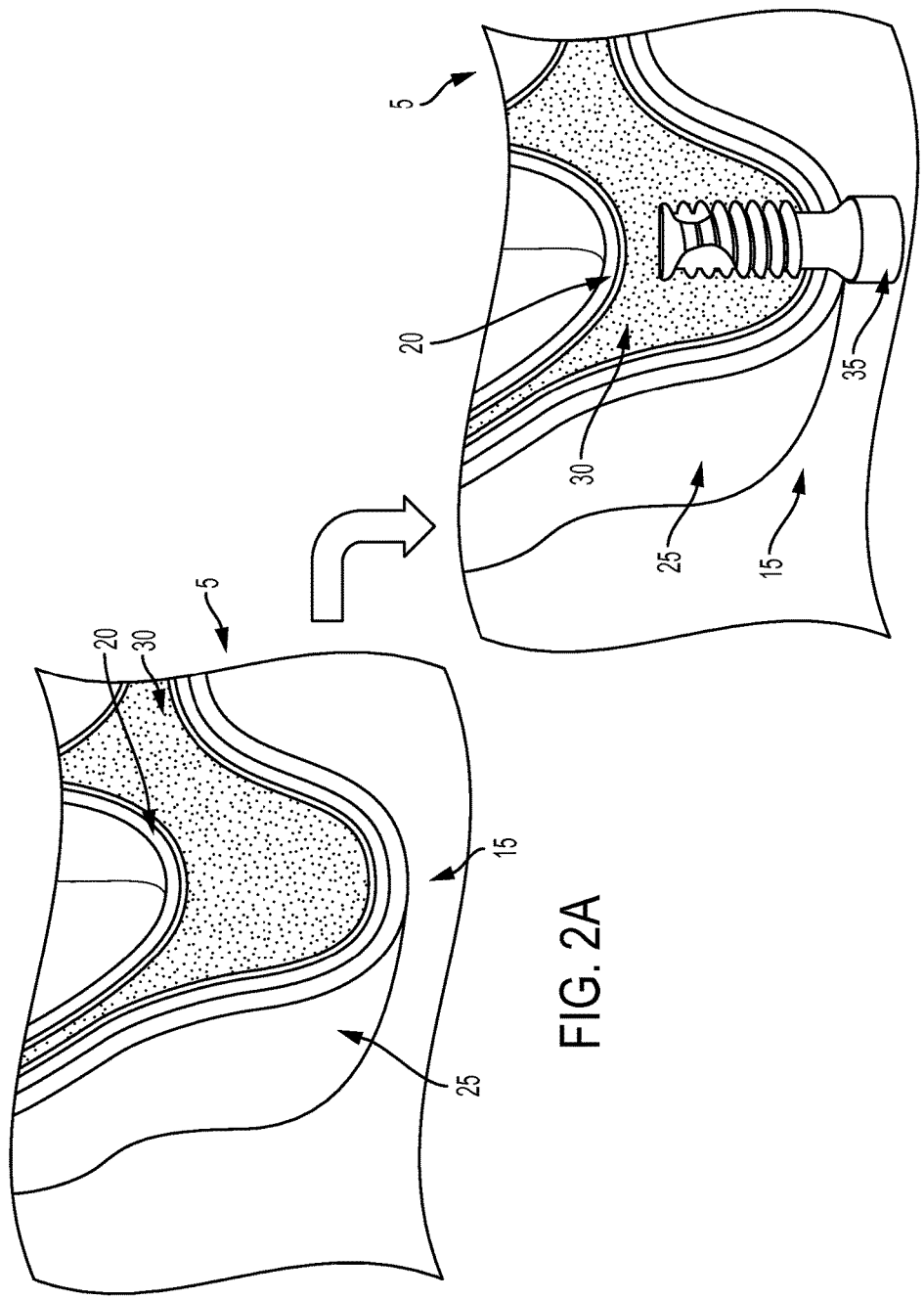

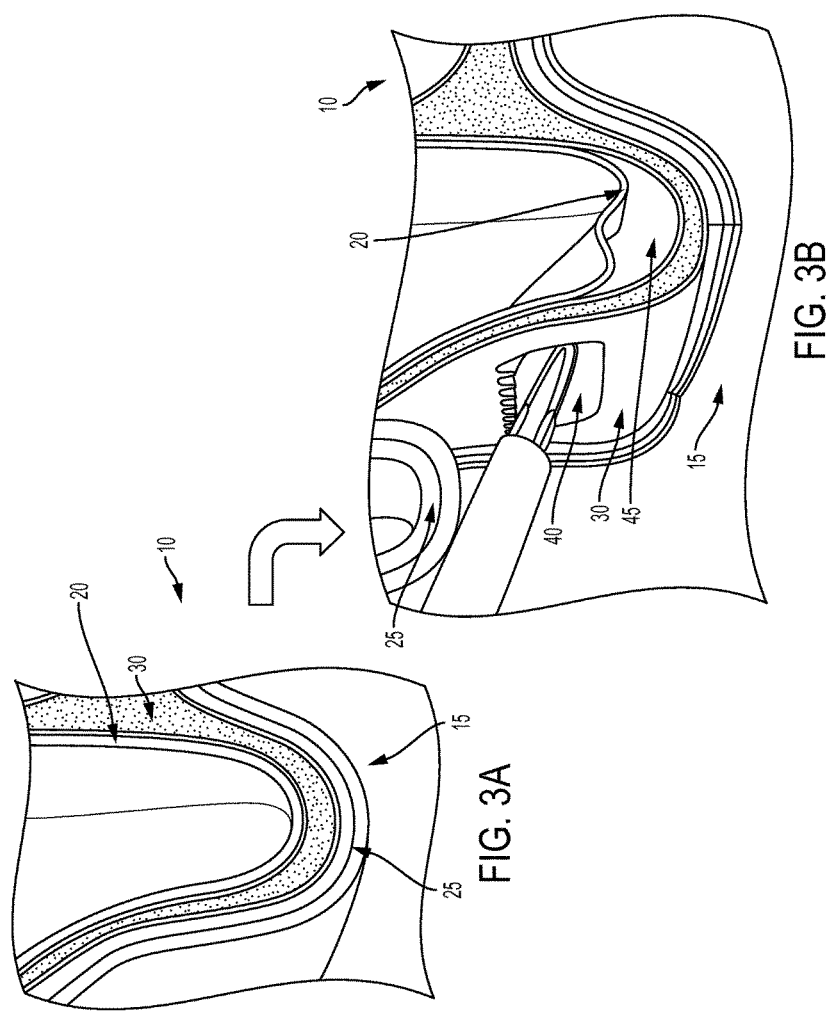

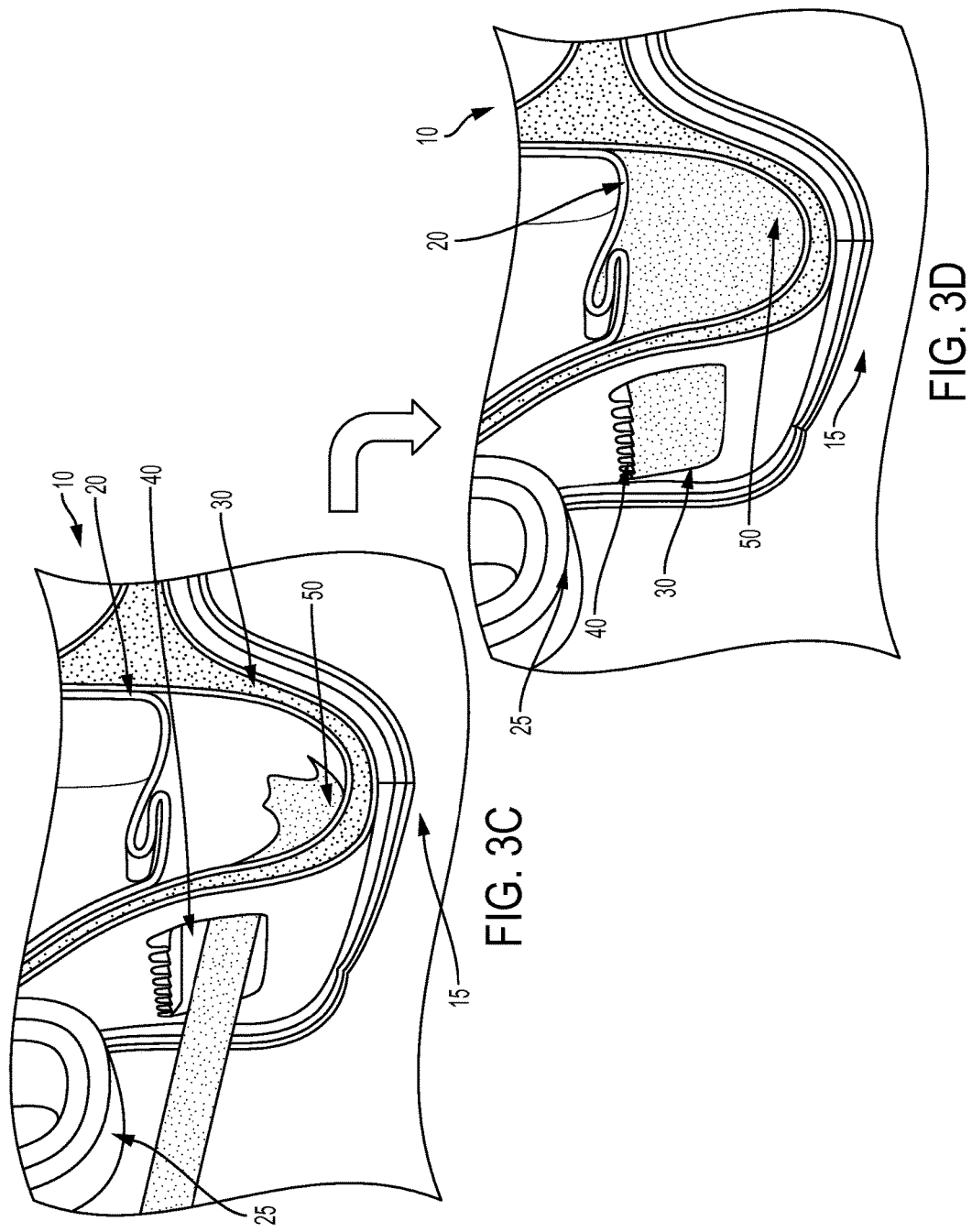

METHOD FOR CONDUCTING A GUIDED SINUS LIFT PROCEDURE

BACKGROUND OF THE DISCLOSURE

Field of the Disclosure

The present disclosure relates to dental implant procedures and, more particularly, to methods and systems for a conducting a guided sinus lift procedure for facilitating implantation of a dental implant.

Description of Related Art

Dental implants rely upon suitable bone structure in relation to the patient's jaw in order to be effective. However, in some instances, a dental implant may be required in a location in the maxilla (i.e., the posterior maxilla or upper jawbone) that may be too close to the lowered floor of the sinus. Lowering of the sinus floor can be caused, for example, by long-term tooth loss without the required treatment, periodontal disease, and/or trauma. In such instances, a sinus augmentation (sinus lift) procedure may be required to raise the floor of the sinus (i.e., an anatomical structure, similar to an air pocket or bubble, located above the maxilla), which could otherwise interfere with placement of a dental implant, and also to avoid perforating sinus membrane during the dental implant procedure. Once the sinus membrane/floor of the sinus is lifted or raised, the recess remaining in the maxilla, may be filled with a suitable material so as to retain the sinus floor in the lofted position, while providing additional bone or bone-like structure in which to implant the dental implant.

In connection with such a sinus augmentation procedure, a window or portal must first be incised from the maxilla so as to allow access to the sinus membrane to perform the lift procedure. With computerized tomography (CT) and other imaging scans becoming more common, the practitioner may be able to graphically visualize the jawbone structure, without or before the invasive incision. However, even though the lowered sinus condition may have first been detected and diagnosed through such various non-invasive imaging techniques as CT, the surgeon must often use a "best estimate" or "best guess" when incising the maxilla to form the window/portal. As such, there may be a risk that the surgeon could perforate the sinus membrane when performing the incision of the maxilla and/or could inadvertently damage other portions of the maxilla.

Thus, there exists a need for a method and system for providing an improved sinus lift procedure that addresses the noted shortcomings of current procedures, and facilitates, for example, effective pre-surgical planning and guidance during the surgical procedure.

BRIEF SUMMARY OF THE DISCLOSURE

The above and other needs are met by the present disclosure which, in one aspect, provides a method of conducting a sinus lift procedure. Such a procedure comprises forming a secure and physical interaction between a fiducial device and a site within a mouth of a patient to form a fiducial marker, and forming a virtual incising plan for incising a portion of a maxilla of the patient, in registration with and with respect to the fiducial marker, for providing access to a sinus membrane therethrough. Movement of an incising device is then physically regulated with respect to the fiducial marker, with a guidance device operably engaged with the incising device. The incising device is in physical communication with the fiducial marker via the fiducial device, and the guidance device is configured to physically regulate movement of the incising device, in accordance with the virtual incising plan and in correspondence with physical manipulation of the incising device by a user, to incise the portion of the maxilla. Tactile feedback is provided to the user, via the incising device, if the physical manipulation of the incising device by the user deviates from the virtual incising plan.

Various other aspects of the present disclosure are directed to systems for facilitating the disclosed methods of conducting a sinus lift procedure.

Aspects of the present disclosure thus provide apparent advantages as otherwise detailed herein.

BRIEF DESCRIPTION OF THE SEVERAL VIEWS OF THE DRAWING(S)

Figure 4:
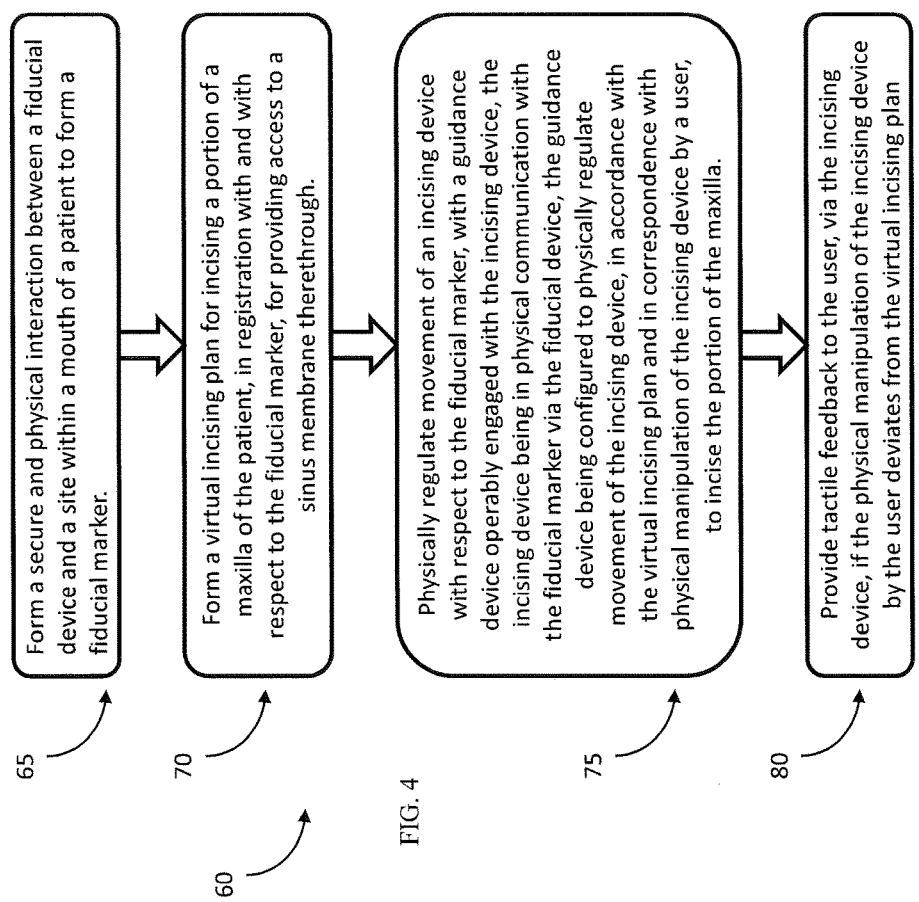
Figure 5:
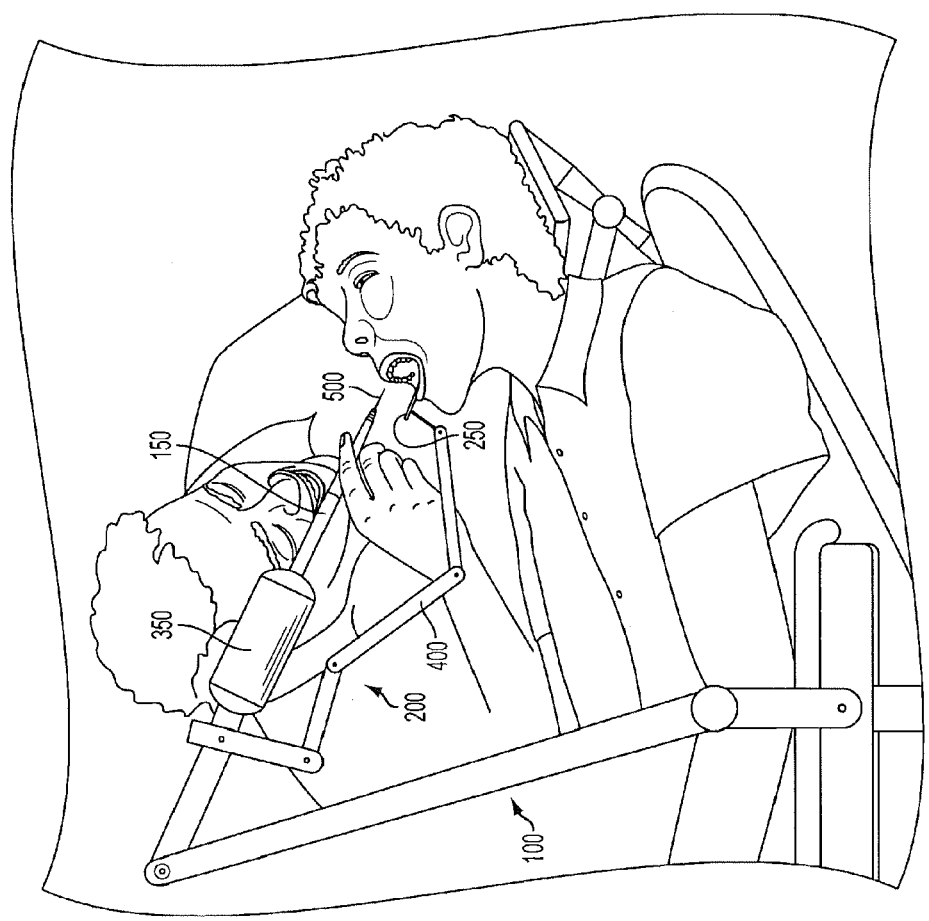
Figure 6:
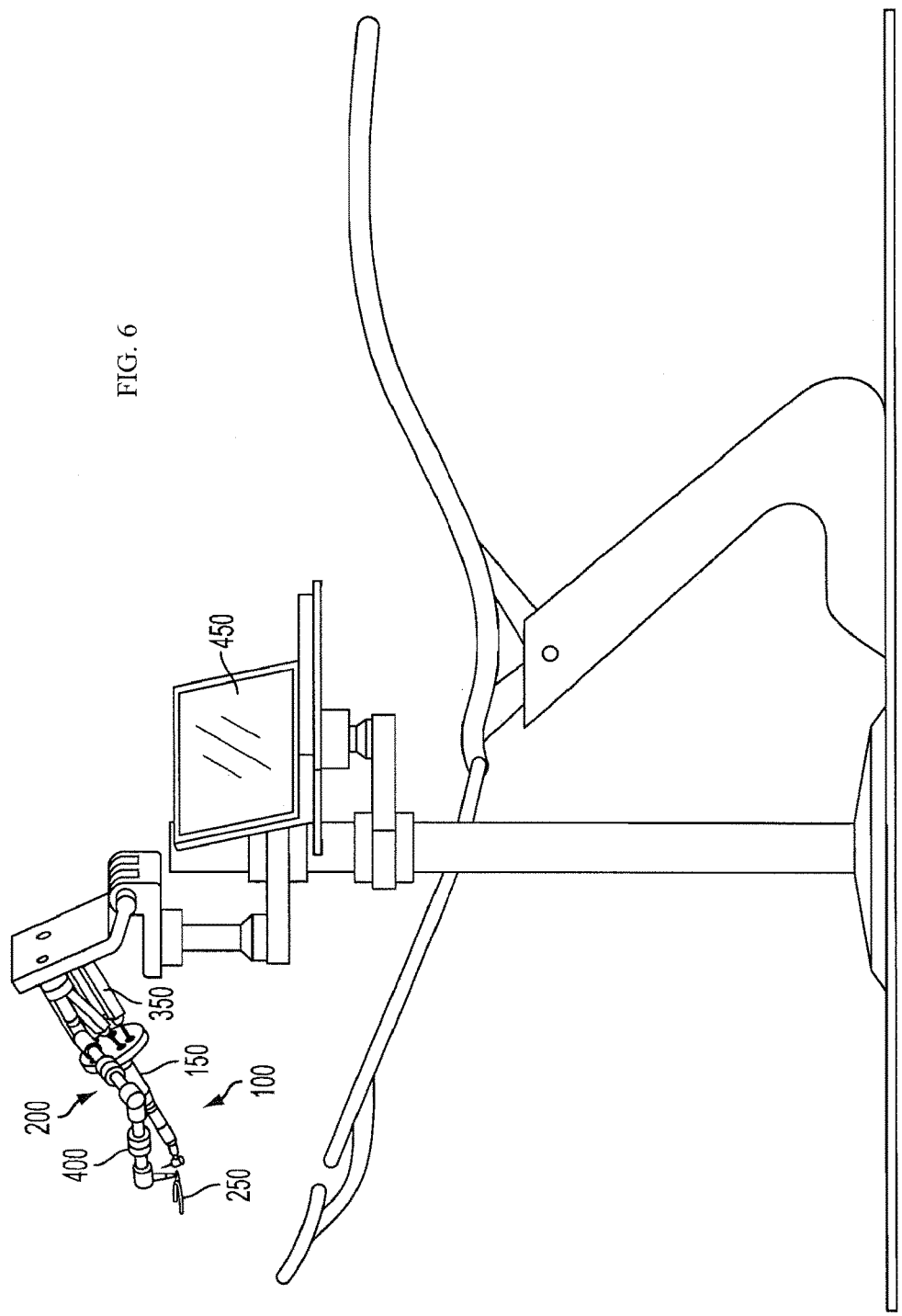
Figure 7:
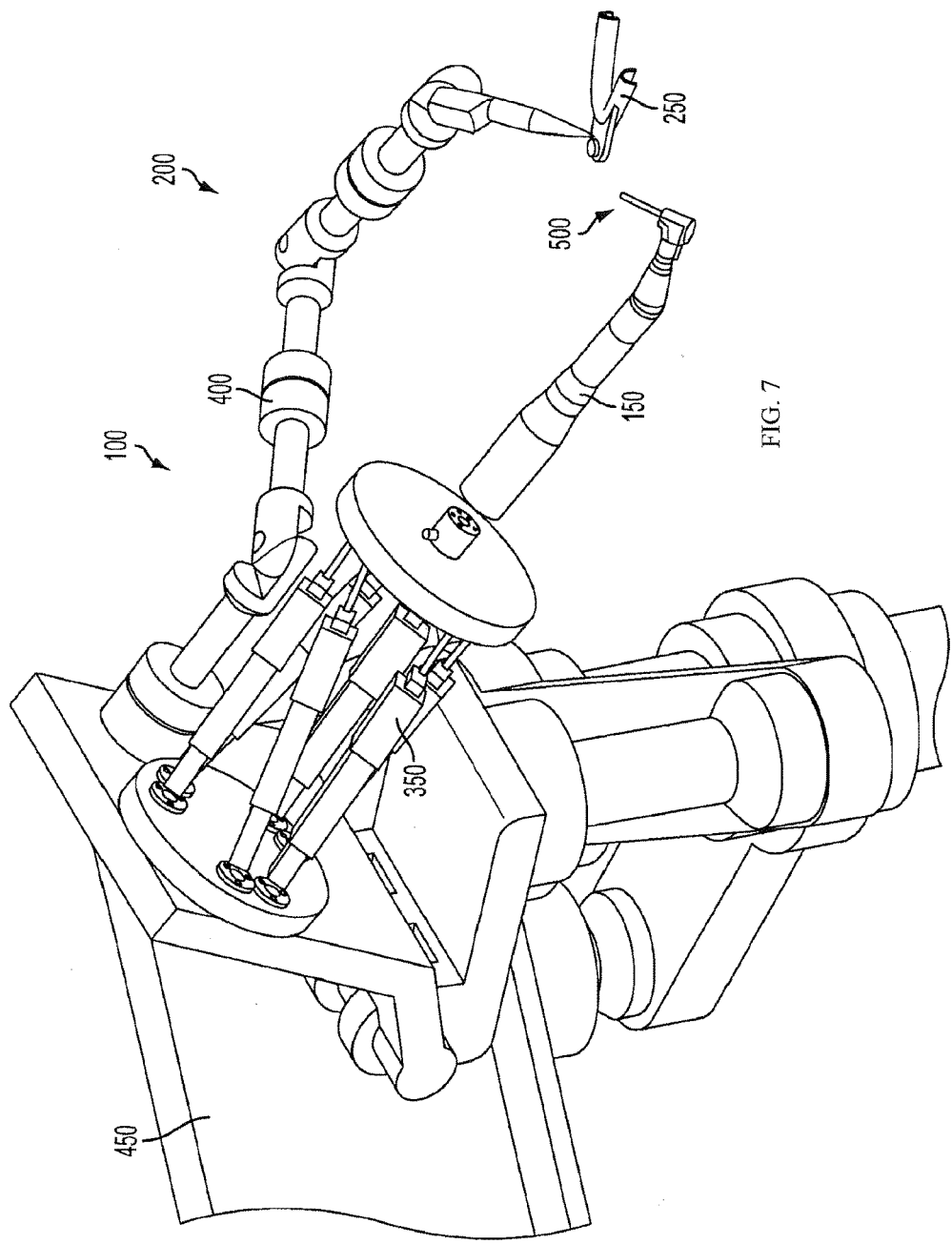

Having thus described the disclosure in general terms, reference will now be made to the accompanying drawings, which are not necessarily drawn to scale, and wherein:

FIG. 1 schematically illustrates a normal sinus in comparison to an expanded sinus;

FIGS. 2A and 2B schematically illustrate an implantation of a dental implant in the bone structure of a maxilla having a normal sinus configuration;

FIGS. 3A-3D schematically illustrate a sinus lift procedure performed in a maxilla having an expanded sinus configuration;

FIG. 4 schematically illustrates a flow of a method for conducting a sinus lift procedure, according to one aspect of the present disclosure;

FIG. 5 schematically illustrates a system for conducting a sinus lift procedure according to one aspect of the present disclosure; and FIGS. 6 and 7 schematically illustrate a system for conducting a sinus lift procedure according to an alternate aspect of the present disclosure.

DETAILED DESCRIPTION OF THE DISCLOSURE

The present disclosure now will be described more fully hereinafter with reference to the accompanying drawings, in which some, but not all embodiments of the disclosures are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

Aspects of the present disclosure are directed to methods of conducting a sinus lift or sinus augmentation procedure, when necessary or desired to facilitate a secure site with regard to the maxilla for implanting a dental implant, while minimizing or eliminating risk of damage to the sinus.

FIG. 1 schematically illustrates a side-by-side comparison of a "normal" sinus condition 5 with respect to the maxilla 15 of a patient, with a sinus having a lowered floor (otherwise referred to as an "expanded sinus") 10. In general, should the patient with a "normal" sinus condition 5 (see, e.g., FIG. 2A) require a dental implant 35, there will likely be sufficient bone structure 30 in the maxilla 15 to perform the implantation procedure (see, e.g., FIG. 2B in which an anchor structure for a dental implant 35 has been implanted in the maxilla 15).

A lowered sinus floor may be discovered (see, e.g., FIG. 3A), for example, through pre-procedure imaging or other diagnostic technique (i.e., computerized tomography (CT)

and other imaging scans), which may indicate to the surgeon that the sinus lift procedure is required before the intended implantation of a dental implant can occur. In the vicinity of the intended dental implant requiring the sinus lift, the surgeon must first resect the gum tissue 25 covering the maxilla 15, and then cut a small window or portal 40 in the bone structure 30 of the maxilla 15 (i.e., the side of the maxilla ridge adjacent to the sinus—see, e.g., FIG. 3B), while preferably avoiding damage to the sinus membrane 20 generally disposed adjacent to the opposing side of the bone structure 30 of the maxilla 15. Through this window/portal 40, as shown, for example, in FIG. 3B, the surgeon can then raise the sinus floor (i.e., the low portion of the sinus membrane 20) and retain it at a sufficiently raised level to allow the remaining cavity or recess 45 within the maxilla 15 to be filled with an appropriate substance 50, preferably a bone substance or bone-like substance such as, for example, autogenous, cadaveric, bovine or simulated bone (see, e.g., FIGS. 3C and 3D). The fill substance 50, once cured, may then supplement the existing bone 30 of the maxilla 15 (see, e.g., FIG. 3D) to provide sufficient bone structure in which to perform an implantation procedure for the dental implant 35. In some instances, the surgeon may use the window/portal 40 to monitor the interior of the maxilla 15, while the bore for the intended dental implant 35 is formed (i.e., drilled) in the maxilla ridge and the dental implant 35, or anchor associated therewith, is implanted in the formed bore (see, e.g., FIG. 2B). In such instances, drilling the bore for the dental implant becomes a relatively low risk procedure (i.e., a relatively low risk of perforating the sinus membrane) since the interior of the maxilla may be visible through the window/portal 40, and/or the sinus membrane 20 may be raised and maintained at a sufficient distance from the intended location of the dental implant bore.

Aspects of the present disclosure are thus directed to and address a method of conducting a sinus lift procedure which addresses the limitations noted herein. More particularly, aspects of the present disclosure implement pre-procedure virtual incision planning in conjunction with physically guided robotic assistance in at least the incising portion of a sinus lift procedure, and haptic or tactile feedback to the surgeon via an incising device physically engaged with and guided by the robotic assistance. Forming the window/portal for accessing the sinus membrane 20 may require the window/portal 40 to be incised in the bone structure of the maxilla 15. That is, the sinus membrane 20 may be disposed immediately adjacent to the interior surface of the bone structure 30 of the maxilla 15, and forming the window/portal 40, for instance, with a drill or boring bit, may result in the risk of perforating the sinus membrane 20 with the tip of the bit. As such, the risk of perforating the sinus membrane 20 may be reduced by incising the window/portal 40 in the bone structure 30 using an appropriate incising device. The incised window/portal 40 may be round in shape, in some instances, though given the structure of the maxilla in the area to be accessed (i.e., greater in length than in height), the incised window/portal 40 may preferably be noncircular. In particular instances, the window/portal 40 may be incised as an oval (i.e., an oval having the major axis thereof substantially parallel to the maxilla ridge. In other instances, the incised window/portal 40 may be square or rectangular (i.e., a rectangle having the major dimension thereof substantially parallel to the maxilla ridge). In this regard, the parameters (i.e., directions of incising motions, the length of each incision, and the depth of each incision) with respect to incising a window/portal 40 in this manner are generally more complex than guiding a drill device to bore a circular hole, as will be appreciated by one skilled in the art.

Accordingly, aspects of the present disclosure, as shown, for example, in FIG. 4, comprise a method of conducting a sinus lift procedure 60. Such a procedure may comprise, for example, forming a secure and physical interaction between a fiducial device and a site within a mouth of a patient to form a fiducial marker (block 65), and forming a virtual incising plan for incising a portion of a maxilla of the patient, in registration with and with respect to the fiducial marker, for providing access to a sinus membrane therethrough (block 70). Movement of an incising device is then physically regulated with respect to the fiducial marker, with a guidance device operably engaged with the incising device (block 75). The incising device is in physical communication with the fiducial marker via the fiducial device, and the guidance device is configured to physically regulate movement of the incising device, in accordance with the virtual incising plan and in correspondence with physical manipulation of the incising device by a user, to incise the portion of the maxilla to form the window/portal. Tactile feedback is provided to the user, via the incising device, if the physical manipulation of the incising device by the user deviates from the virtual incising plan (block 80).

FIGS. 5-7 illustrate systems which may facilitate pre-procedure virtual incision planning in conjunction with physically guided robotic assistance in at least the incising portion of a sinus lift procedure, and haptic or tactile feedback to the surgeon via an incising device physically engaged with and guided by the robotic assistance, according to the present disclosure, the systems being generally indicated by the numeral 100. Such systems 100 may be similar to dental implantation systems as disclosed, for example, in U.S. Patent Application Publication No. US 2009/0253095 to Salcedo et al. and assigned to Neocis Inc., also the assignee of the present application. US 2009/0253095 is thus incorporated herein by reference in its entirety.

As previously disclosed, one aspect of the sinus lift procedure disclosed herein may generally involve a pre-procedure imaging step, wherein CT, MRI, x-ray, or other appropriate imaging of the patient's jaw/maxilla structure may be obtained, and any anomalies diagnosed (i.e., whether the sinus is expanded and/or whether there is insufficient bone structure for receiving a dental implant). In such instances where a sinus lift procedure may be prescribed by the pre-procedure imaging prior to placing a dental implant in the corresponding area of the maxilla, a secure and physical interaction between a fiducial device and a site within a mouth of a patient may be established to form a fiducial marker. Such fiducial device may comprise or otherwise be associated with, for example, a splint 250 configured to engage the patient's mouth in a "firm" or secure interaction (i.e., the splint 250 is engaged with the patient's teeth and does not move with respect to the patient's mouth), as shown in FIGS. 5 and 6. In one aspect, the positioning of the splint 250 with respect to the patient's mouth may not be critical or important, as long as the splint 250 remains rigidly in place. One skilled in the art will further appreciate that there may be many other types of fiducial devices and/or manners in which to form a fiducial marker with respect to the patient's mouth, as disclosed, for example, in US 2009/0253095. In some instances, the fiducial marker may be preferably configured to have a geometry or other characteristic or feature that uniquely defines the fiducial marker in a three-dimensional space (i.e., such that the fiducial marker is readily identified in images of the patient's jawbone structure). In such instances, the fiducial marker may be comprised of, for example, a radiopaque material that can be clearly defined in the image (e.g., CT or MRI).

The fiducial device or suitable substitute (i.e., a imageable marker that may be interchangeable with the physical fiducial device to form/define the fiducial marker), may be used when imaging the maxilla and/or to form a virtual incising plan for incising a portion of the maxilla of the patient to form the window/portal for accessing the sinus membrane therein to conduct the sinus lift procedure. With the fiducial marker involved in the imaging of the maxilla, the virtual incising plan may thus be formed in registration with and with respect to the fiducial marker, and particularly directed to facilitating incision of the window/portal in the maxilla for providing access to the sinus membrane therethrough. The imaging procedure may provide data for the virtual incising plan with respect to, for example, the location on the maxilla 15 for suitable access to the sinus membrane 20, the amount and location of the overlying gum tissue 25 that must first be resected, and/or the location and/or shape and/or dimension(s) and/or depth and/or order of the required incision(s). Accordingly, relevant parameters may be included in the virtual incising plan, and determined, in some instances, relative to the fiducial marker.

The virtual incising plan may then be integrated or otherwise associated with an appropriate robotic assistance system, such as system 100, having an appropriate incising device, such as a cutting device 150, operably engaged therewith. The robotic assistance system 100 may include, for instance, a guidance device 200 in physical communication with and between the fiducial device (i.e., splint 250) and the incising device (i.e. cutting device 150). The guidance device 200, in some aspects, may comprise an articulating arm member 350 (i.e., a robotic arm) which determines a range of motion of the cutting device 150 and/or a communication element 400 in communication between the splint 250 and the cutting device 150 and/or the arm member 350. For example, the communication element 400 may comprise a mechanical linkage connecting the splint 250 to the cutting device 150/arm member 350. That is, the communication element 400 may comprise, for example, a mechanically-tracked arm which attaches to the splint 250 engaged with the patient. In some instances, the arm may be attached to the splint 250 (rigidly and in a known, repeatable manner) with an attachment mechanism comprising a kinematic mount. Attached to the patient in this manner via the attachment mechanism and the splint 250, the communication element 400 provides data (whether constantly, selectively, or otherwise as necessary) about the position of the patient (i.e., with respect to the fiduciary marker) to the cutting device 150/arm member 350, while still providing for accurate guidance thereof in the event that the patient moves.

However, one skilled in the art will appreciate that the splint 250 and/or the fiducial marker associated therewith may be communicated to the cutting device 150/arm member 350 in many different manners. For example, the fiducial marker may be communicated via a communication element 400 comprising a wireless transceiver, a hardwire connection, an optical communication system, or any other suitable mechanism, whether electrical, mechanical, electromechanical, or optical in nature. In any instance, the guidance device 200 may be further configured to include a controller device 450 (i.e., a computer device as shown in FIGS. 6 and 7) for registering the fiducial marker from the image of the patient's mouth, in some instances in association with the splint 250 disposed therein, and for appropriately executing the virtual incising plan with respect to the fiducial marker and/or otherwise communicating the fiducial marker to the cutting device 150/arm member 350, and physically regulating movement of the cutting device 150/arm member 350 in accordance with the virtual incising plan.

In one aspect, the controller device 450 may be further configured to receive the image of the patient's jawbone/maxilla structure having the fiducial marker associated therewith. In some instances, the controller device 450 may be further configured to be capable of executing an incising routine that may comprise software, hardware, or a combination thereof. The incising routine may allow the practitioner to create, for example, the virtual incising plan based on the captured image, whether in two dimensions or three dimensions, and to manipulate the image(s) of the patient's jawbone structure in conjunction with a "virtual procedure" in order to develop the virtual incising plan for creating the window/portal for the sinus lift procedure for the patient in conjunction with a computerized model based on the image(s). In some aspects, the incising routine/process and/or virtual incising plan may be created in relation, for example, to a coordinate system (relative or absolute), as will be appreciated by one skilled in the art, for associating the incising parameters with the fiducial marker. In other aspects, the controller device 450 may include a peripheral device (i.e., a trackball or joystick in conjunction with, for example, 3D goggles, all not shown) to assist with or otherwise permit virtual manipulation of the incision(s) with respect to the image(s) in order to, for example, determine an appropriate shape, size, and placement of the required window/portal for accessing the sinus membrane relative to the jawbone/maxilla structure. The controller device 450 may be further configured to perform such manipulation manually, automatically, or semi-automatically, as necessary or desired.

In aspects where the splint 250/fiducial marker approach is used, the mouth of the patient is automatically registered with the system 100 once the communication element 400 (arm) is attached to the splint 250 via the kinematic mount of the attachment mechanism. That is, the fiducial marker is automatically determined from the image(s) of the patient's jawbone structure, and the alignment and location thereof in physical space is known due to the kinematic mount connecting the arm to the splint 250. In any instance, the communication element 400 is configured to engage the arm member 350 in a manner known to the system 100, such that the position/movement characteristics of the end effector of the arm 350 are also known. This communication between the communication element 400 and the arm member 350 thus allows the cutting device 150 to be registered with respect to the fiducial marker (or other reference with respect to the patient) attached to the patient via the splint 250, the kinematic mount, the communication element 400, and the arm member 350. In one particular aspect, the system 100 thus disclosed herein may be configured to form a physical communication between the fiducial marker (i.e., by way of a physical engagement with a fiducial device forming the fiducial marker or otherwise having the fiducial marker associated therewith) and the interacting portion 500 (i.e., the cutting tip of the cutting device 150) of the cutting device 150 engaged with the end effector of the arm 350. In this manner, the virtual incising process/plan, planned through the controller device 450, may be accomplished in relation to and in registration with the fiducial marker (or other reference with respect to the patient) and thus translated or otherwise communicated to the system 100 for physically regulating the movement of the cutting device 150.

The cutting device 150 is disposed in or otherwise engaged with the end effector of the arm member 350 (robotic arm). The arm member 350 may be configured, for example, to provide six degrees of freedom and can also be configured to restrict or otherwise control the movement of the cutting device 150. For example, the arm member 350 may be configured to include any number of mechanisms, arrangements, or provisions, that may restrict or regulate the freedom of motion of the arm 350 in particular direction, while freely or unrestrictedly allowing freedom of motion in other particular directions (i.e., restricted freedom of motion when the motion of the end effector/cutting device 150 deviates from the virtual incising plan, but unrestricted freedom of motion when the motion of the end effector/cutting device 150 is moved in accordance with the virtual incising plan). The arm member 350 may have a miniature parallel structure to which the cutting device 150 is secured and allowed to have full freedom of movement when not in cutting mode. Since the cutting device 150 is attached to the end effector of the arm member 350, the patient interacting portion (i.e., the cutting tip) 500 (see, e.g., FIGS. 5 and 7) of the cutting device 150 must be in a known position (i.e., known to the system 100) relative to the arm member 350. In some aspects, in order to calibrate the interacting portion 500 of the cutting device 150 with respect to the fiducial marker, a calibration element may be engaged with the cutting device 150 via a kinematic coupling (i.e., rigidly mounted thereto in a known, repeatable manner). One skilled in the art will thus appreciate that the interacting portion 500 of the cutting device 150 can then be calibrated with various tip calibrating methods (i.e., invariant point, etc.). Once calibrated, the calibration element is replaced with a cutting element or tip in the cutting device 150, in a known and repeatable manner, so that the calibration parameters (i.e., the position of the distal-most point and axis of cutting) associated with the interacting portion 500 are maintained as calibrated.

With the alignment with respect to the patient established and known by the system 100, and the virtual incising plan developed through the controller device 450, the gum material resection, and the window/portal formation for the sinus lift procedure can then be initiated by the practitioner physically engaging (i.e., grasping) and moving the cutting device 150 toward the patient's mouth (having the splint 250 engaged therewith). In such instances, the controller device 450 is configured to control or regulate the movement of the cutting device 150 via the arm member 350 such that the action by the practitioner only allows the interacting portion 500 (i.e., the cutting tip) to move to the appropriate starting position for the incising procedure, with respect to the patient's jawbone structure, as determined by the controller device 450 and dictated by the virtual incising plan. For example, the controller device 450 executing or following the virtual incising plan may regulate or control movement of the cutting device 150 by providing unrestricted movement of the cutting device 150 by the practitioner toward the mouth of the patient, but may prevent motion of the cutting device 150 in a direction toward a portion of the patient's body other than the mouth area (i.e., by locking a joint or otherwise providing resistance to the practitioner moving the cutting device in a direction that deviates from the virtual incising plan). Such regulation or control of the movement of the cutting device 150 via the arm 350 may be physically sensed by the practitioner (i.e., as tactile or haptic feedback through the grasp of the cutting device 150).

Once the cutting element is in the start position dictated by the controller device 450, the invasive (incising) portion of the sinus lift procedure can then be initiated, wherein the controller device 450 may further dictate other parameters of the cutting device 150 such as, for example, the orientation of the path of the cutting element and/or the cutting direction/distance/depth from the cutting origin, also according to the virtual incising plan. One skilled in the art will appreciate that the cutting device 150 may be guided according to the virtual incising plan to perform the incision of the entire window/portal in the maxilla. However, in other instances, the cutting device 10 may be guided so as to incise particular boundary elements of the window/portal. For example, where the desired window/portal is a square or rectangle, the cutting device 150 may be guided to incise only the four corners of that window/portal (i.e., to indicate the location/size/shape/etc. of the desired window/portal), wherein the completion of the incision(s) may then be manually performed by the practitioner independently of the system 100.

During the incising procedure, tactile or haptic feedback may be provided to the user, via the user's grasp of the incising device, if the physical manipulation of the incising device by the user deviates from the virtual incising plan. In these instances, system 100 allows unrestricted movement of the cutting device 150, as guided by the practitioner, in accordance with the virtual incising plan and implemented via the controller device 450 and the arm member 350. That is, the system 100 may be configured to restrict movement of the cutting device 150, if the manipulation of the cutting device 150 by the practitioner deviates from the virtual incising plan. For instance, the system 100 may be configured for restricted movement of the arm member 350/cutting device 150, as communicated to the practitioner through tactile or haptic feedback via the practitioner's grasp of the cutting device 150, where, for example, the arm member 350/cutting device 150 may be easier to move according to the virtual incising plan, and more difficult to move if deviating from the virtual incising plan. In other instances, various forms of tactile, haptic, or other feedback may be provided to the practitioner, whether through the cutting device or otherwise. For example, the cutting device 150 may be configured to vibrate in the practitioner's hand if the cutting tip deviates from the virtual incising plan. In other instances, the cutting tip may not function if a deviation from the virtual incising plan is detected. In still other instances, an audible tone or tactile vibration may be emitted from a device separate from the cutting device 150 (i.e., the arm 350 may be vibrated and/or the system 100 may otherwise include an audible alarm). As such, one skilled in the art will appreciate that the system 100 may be further configured to provide other manners of feedback (tactile, haptic, or otherwise) to the practitioner such as, for example, via a deviation warning indicia or other indicator, or any other suitable audio and/or visual mechanism. Therefore, the system 100 includes provisions for actually implementing the virtual incising plan, physically regulating movement of the cutting device, and providing tactile/haptic feedback directly to the practitioner via the cutting device, and thus facilitates an improved incising procedure for forming the necessary window/portal for a sinus augmentation, rather than merely warning the practitioner if any procedural parameters may be inaccurate or requiring the practitioner to manually follow a pathway displayed on a screen. One skilled in the art will also appreciate, however, that, in some instances, the system 100 may be further configured to autonomously accomplish the virtual implantation plan, without the manipulation of the practitioner, through automatic manipulation of the arm member 350/cutting device 150 via the controller device 450. One skilled in the art will further appreciate that aspects of the system 100 disclosed herein may also be implemented to perform a dental implant procedure (i.e., as disclosed in US 2009/0253095 incorporated herein by reference) subsequent to the sinus augmentation procedure disclosed herein, and that the involvement of the system may provide additional advantages and benefits to those disclosed herein.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of conducting a sinus lift procedure, comprising:

forming a secure and physical interaction between a fiducial device and a site within a mouth of a patient to form a fiducial marker;

forming a virtual incising plan for incising a side portion of a maxilla of the patient, in registration with and with respect to the fiducial marker, for providing access to a sinus membrane through the side portion of the maxilla, the side portion of the maxilla being adjacent to a bottom portion of the maxilla in which a dental implant is implanted;

incising the portion of the maxilla using an incising device, without using a physical guide engaged with the maxilla of the patient, the incising device having movement thereof physically regulated, with respect to the fiducial marker, by a guidance device operably engaged with the incising device, the incising device being in physical communication with the fiducial marker via the guidance device, the guidance device being configured to physically regulate movement of the incising device, in accordance with the virtual incising plan and in correspondence with physical manipulation of the incising device by a user; and providing tactile feedback to the user, via the incising device, if the physical manipulation of the incising device by the user deviates from the virtual incising plan.

2. A method according to claim 1, further comprising imaging the maxilla with respect to the fiducial marker to facilitate registration of the virtual incising plan therewith.

3. A method according to claim 1, wherein providing tactile feedback further comprises allowing movement of the incising device in accordance with the virtual incising plan and physically preventing movement of the incising device deviating from the virtual incising plan.

4. A method according to claim 1, wherein providing tactile feedback further comprises vibrating the incising device if movement of the incising device deviates from the virtual incising plan.

5. A method according to claim 1, further comprising engaging the guidance device with the fiducial device such that the guidance device is physically related with the fiducial marker.

6. A method according to claim 1 wherein physically regulating movement of the incising device further comprises physically regulating movement of the incising device via an arm member physically engaged between the incising device and the fiducial device, the arm member being responsive to the guidance device to guide the physical manipulation of the incising device by the user according to the virtual incising plan.

* * * * *